United States Patent
Peoples, Jr.

(10) Patent No.: US 6,260,761 B1
(45) Date of Patent: Jul. 17, 2001

(54) SYSTEM AND METHOD FOR ACCURATELY DISPENSING PRESCRIPTIONS IN A PHARMACY

(76) Inventor: Max J. Peoples, Jr., 2737 Cooper Ridge Rd., Columbus, OH (US) 43231

( * ) Notice: Subject to any disclaimer, the term of this patent is extended or adjusted under 35 U.S.C. 154(b) by 0 days.

(21) Appl. No.: 09/527,651

(22) Filed: Mar. 17, 2000

Related U.S. Application Data (63) Continuation of application No. 09/085,279, filed on May 27, 1998.
(60) Provisional application No. 60/048,124, filed on May 30, 1997.

(51) Int. Cl.[7] .................................................. G08C 21/00
(52) U.S. Cl. ..................................... 235/462.07; 235/375
(58) Field of Search ........................ 235/462.01, 462.07, 235/462.12, 375, 380, 494

(56) References Cited

U.S. PATENT DOCUMENTS

| | | |
|---|---|---|
| 4,146,175 * | 3/1979 | Daboub et al. ................. 235/462.01 |
| 4,415,802 | 11/1983 | Long . |
| 4,476,381 | 10/1984 | Rubin . |
| 4,835,372 | 5/1989 | Gombrich et al. . |
| 5,164,575 | 11/1992 | Neeley et al. . |
| 5,272,318 | 12/1993 | Gorman . |
| 5,374,813 | 12/1994 | Shipp . |
| 5,381,487 | 1/1995 | Shamos . |
| 5,401,110 | 3/1995 | Neeley . |
| 5,468,110 | 11/1995 | McDonald et al. . |
| 5,502,944 | 4/1996 | Kraft et al. . |
| 5,508,499 | 4/1996 | Ferrario . |
| 5,528,021 | 6/1996 | Lassus et al. . |
| 5,550,734 | 8/1996 | Tarter et al. . |
| 5,592,374 | 1/1997 | Fellegara et al. . |
| 5,597,995 | 1/1997 | Williams et al. . |
| 5,855,395 * | 1/1999 | Foote et al. ............................. 283/67 |
| 5,883,370 * | 3/1999 | Walker et al. ........................ 235/375 |
| 6,021,392 * | 2/2000 | Lester et al. ............................. 705/2 |
| 6,098,892 * | 8/2000 | Peoples, Jr. .......................... 235/494 |

* cited by examiner

Primary Examiner—Karl D. Frech
Assistant Examiner—Daniel St. Cyr
(74) Attorney, Agent, or Firm—Rader, Fishman, Grauer & McGarry, an Office of Rader, Fishman & Grauer PLLC (57) ABSTRACT

A device and method is provided for converting product-specific identification numbers associated with bar code indicia on pharmaceutical products to an industry standard identification number. The process involves reading a bar code indicia, converting the indicia into an input string and standardizing the input string by means of adding or subtracting characters in accordance with rules based on the bar code type and length of the input string. By means of the invention pharmaceutical products of two different sources may be compared to determine if they contain the same drug as determined by the standard identification number. The device can include a removable member for interchanging and updating bar code indicia information rather than reprogramming the device.

24 Claims, 11 Drawing Sheets

SYSTEM AND METHOD FOR ACCURATELY DISPENSING PRESCRIPTIONS IN A PHARMACY

CROSS-REFERENCE TO RELATED APPLICATIONS

This application is a continuation of U.S. patent application Ser. No. 09/085,279, filed May 27, 1998, which claims priority on U.S. application Ser. No. 60/048,124, filed May 30, 1997.

BACKGROUND OF THE INVENTION

1. Field of the Invention

The invention relates to a system and method for accurately dispensing prescriptions in a pharmacy including a conversion of at least one piece of data into a pharmaceutical standard NDC number.

2. Description of Related Art

Figure 1:
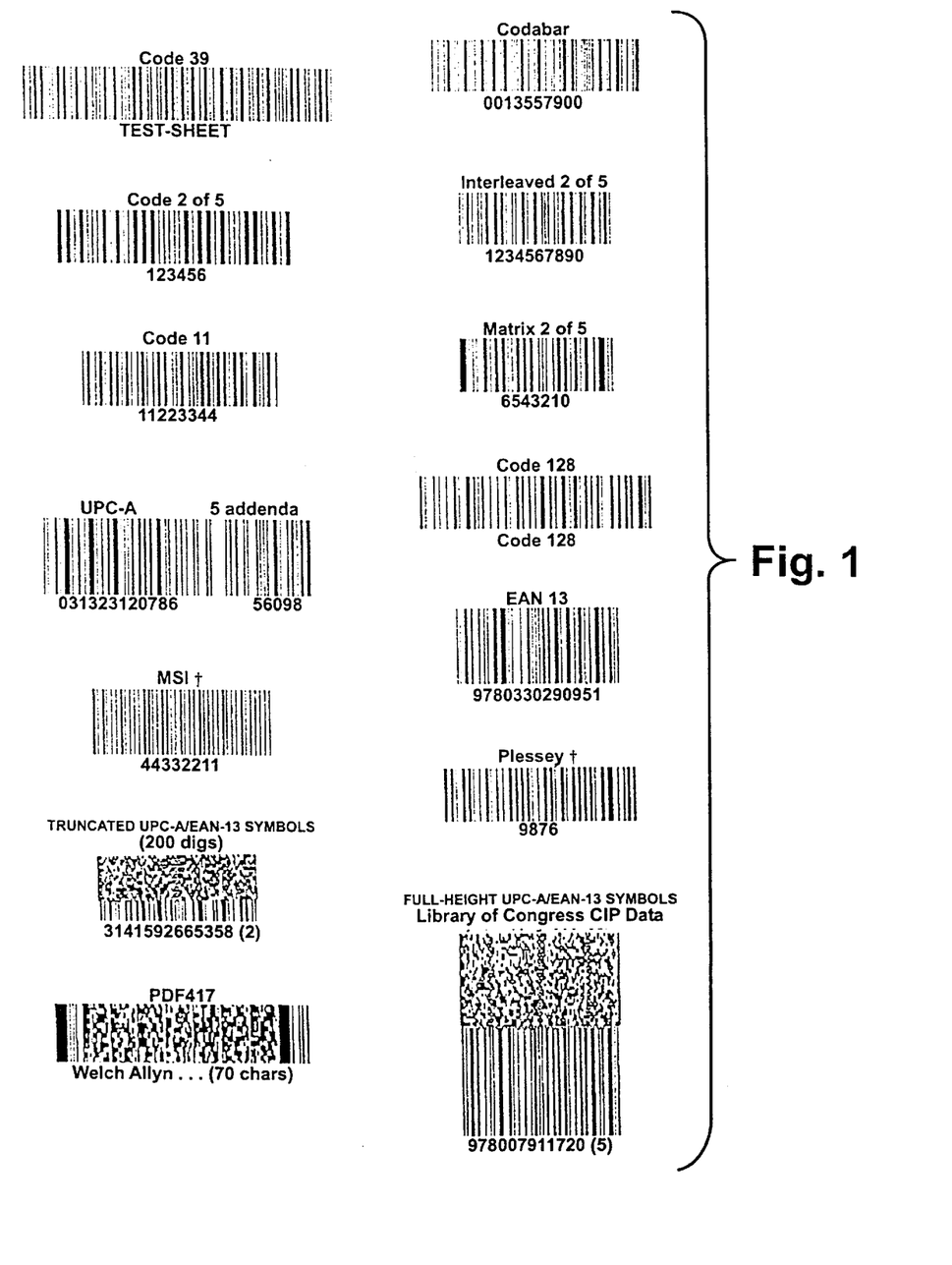
FIG. 1 is a view of several different types of bar codes shown with the name of the type of bar code shown therewith.

Universal Product Code (UPC) symbols are displayed on a myriad of products throughout the country. Often, the UPC symbol is displayed in a "bar code" format, whereby an intermittent pattern of alternating black and white vertical lines of varying widths signifies a string of alphanumeric characters. Bar codes serve as a language which functions to place the string of characters into a machine-readable form. In addition, bar codes have a number of formats which typically must be determined before a machine can read a bar code. FIG. 1 shows examples of different types of bar codes with the generally-accepted name of the type of bar code shown directly above the bar code.

Figure 2:
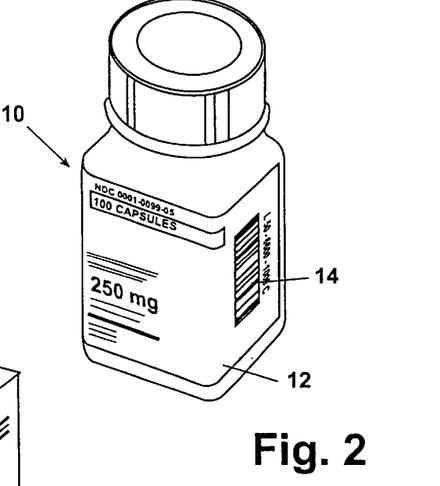
FIG. 2 is a perspective view of a medicine bottle having a bar code thereon.
Figure 3:
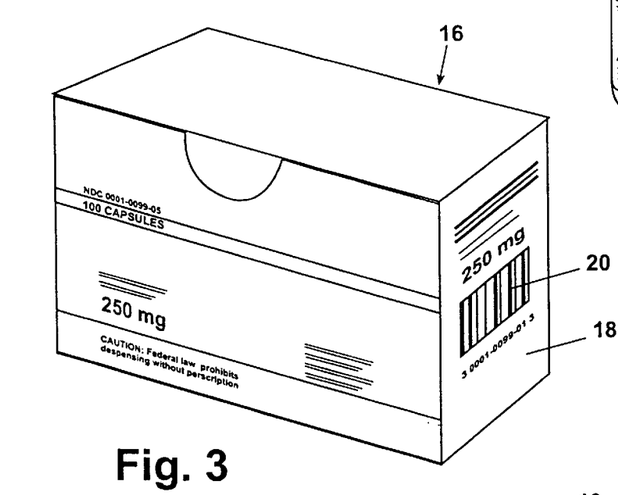
FIG. 3 is a perspective view of a small box having a bar code thereon.
Figure 4:
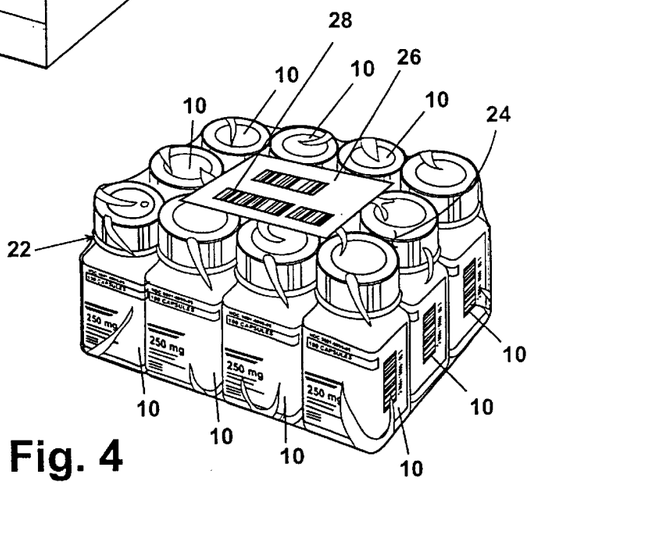
FIG. 4 is a perspective view of a shrink wrapped package of multiple medicine bottles having a bar code thereon.
Figure 5:
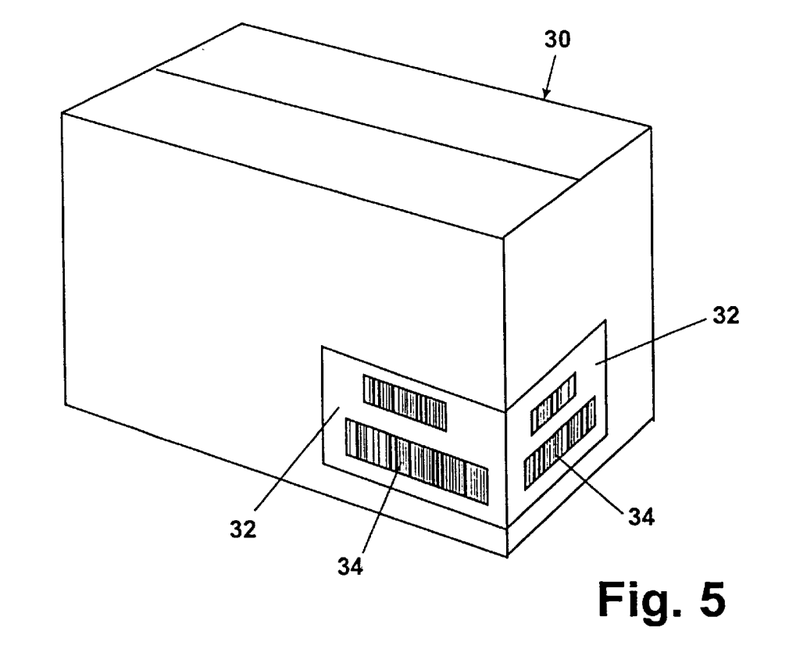
FIG. 5 is a perspective view of a large carton having a bar code thereon.

UPC symbols, in the form of bar codes, are commonly displayed on all kinds of products, including those in the pharmaceutical industry such as medicine containers. FIGS. 2–5 show examples of medicine containers which have been provided with UPC symbols by a product source, such as a manufacturer or distributor. FIG. 2 shows a bottle 10 having a label 12 provided with bar code indicia 14 thereon. FIG. 3 shows a box 16 having a sidewall 18 provided with bar code indicia 20 thereon. FIG. 4 shows a shrink wrapped package 22 of multiple bottles 10 having an upper surface 24 on which a label 26 provided with bar code indicia 28 thereon has been affixed. FIG. 5 shows a carton 30 having a label 32 provided with bar code indicia 34 thereon.

Figure 6:
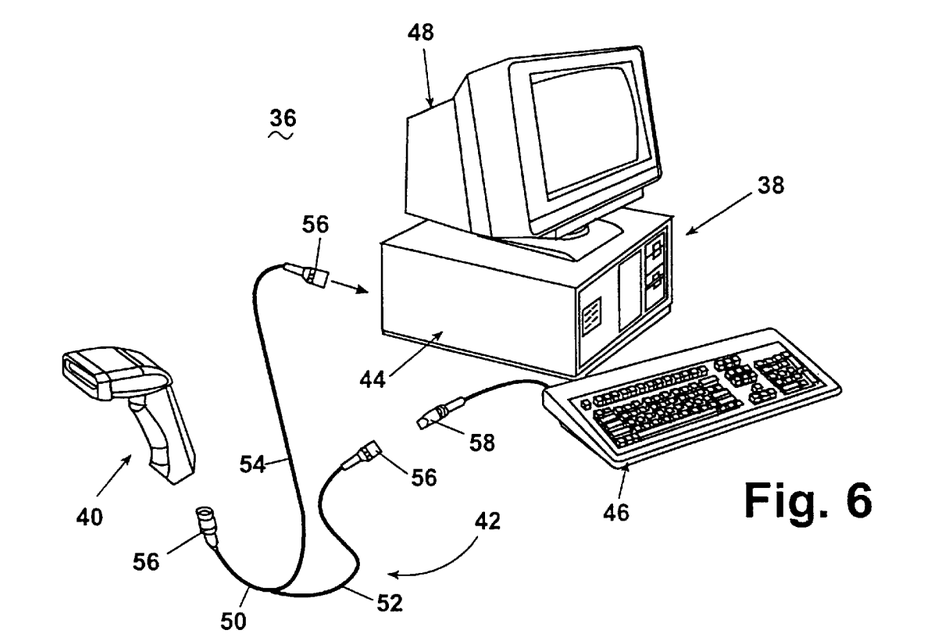
FIG. 6 is a perspective view of a typical computer system incorporating a scanner therein.

Bar codes are typically read by a device called a "scanner." An example of a system which includes a scanner is shown in FIG. 6. The system, shown generally by reference numeral 36, comprises a computer 38 and a scanner 40 interconnected by a conduit 42. The computer 38 generally comprises a processing unit 44, a keyboard 46 and a monitor 48. It will be understood that the monitor 48 and the processing unit 44 are interconnected in a manner well known in the art. The conduit 42 comprises a Y-shaped cable having first, second and third portions 50, 52 and 54, respectively, each provided with a suitable connector 56 at a distal end.

The scanner 40 is typically interconnected intermediate the keyboard 46 and the processing unit 44 by the conduit 42. For example, the connector 56 on the first portion 50 is interconnected to a suitable socket (not shown) on the scanner 40. The connector 56 on the second portion 52 is interconnected to a suitable socket 58 on the keyboard 46. The connector 56 of the third portion 54 is interconnected to a suitable socket (not shown) on the processing unit 44.

Figure 7:
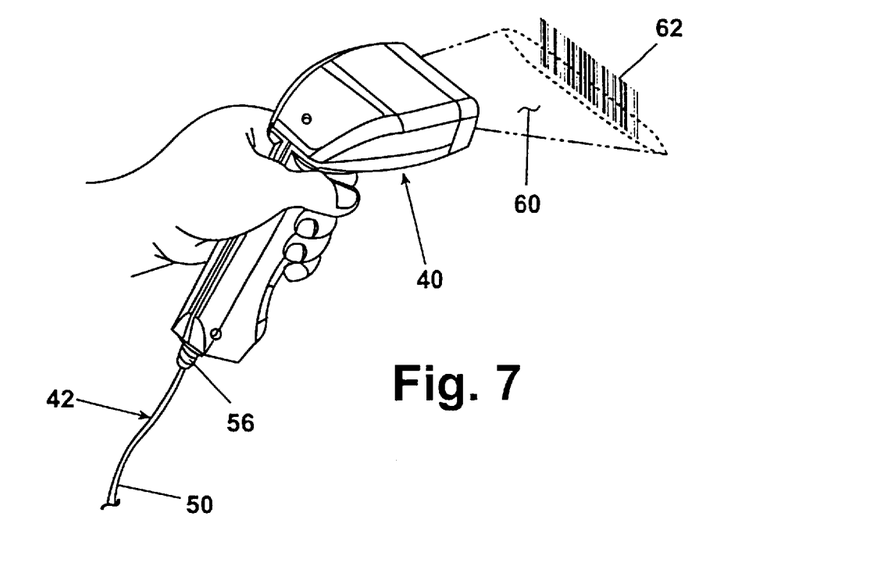
FIG. 7 is a perspective view of a prior art scanning device shown reading a typical bar code.

Thus, signals can be provided to the processing unit 44 by either the keyboard 46 through the portions 50–54 or by the scanner 40 through the portions 50 and 54. FIG. 7 shows the operation of the scanner 40. The scanner 40 typically includes an illumination emitting device therein, such as a laser or intense light, which is actuatable by a trigger (not shown). When the trigger is depressed, a beam 60 is oscillated across a bar code 62. desired to be read. The bar code 62 is converted to an alphanumeric signal by the scanner 40 and sent through the conduit 42 to the processing unit 44. Because the scanner 40 is interconnected intermediate the keyboard 46 and the processing unit 44 and is able to generate alphanumeric characters, the scanner 40 acts as a "second keyboard," providing alphanumeric input to the processing unit 44.

As shown in FIGS. 2–5, bar codes in the form of UPC symbols are marked on packaging for medicine and other pharmaceuticals. With continuing pressure to reduce health care costs there is a need to use technology to improve the quality and accuracy of pharmaceutical distribution. The National Drug Code (NDC) was developed as a universal identification system for pharmaceutical products distributed in the U.S. Since 1969, the Food and Drug Administration (FDA) has required that all drug products be identified clearly with the NDC, which provides pharmaceutical products with a unique all-numeric system identifying the pharmaceutical source, product and package size. Because the industry uses the NDC to order, track and report on pharmaceutical products, bar coding of this number has provided a faster and more accurate way to move both products and information.

The NDC for prescription pharmaceuticals is the single basic identifier for all forms of pharmaceutical products in the health industry. Pharmacy computer systems, third-party prescription claims processing, and sale tracking, reporting and industry support services typically use the NDC to identify, describe and pay for pharmaceutical services. For pharmacy providers, legislation now mandates the use of the NDC for all Medicaid claims. The Department of Justice and the Drug Enforcement Administration require monthly reporting of all incoming and outgoing controlled substance transactions and inventories on a system which mandates use of NDC numbers. From drug manufacturer to wholesaler to drug provider, computer systems are often required to depend on NDC numbers for identifying what is being ordered, paid, returned and credited. It is a proven method of enhancing the efficiency and accuracy of pharmaceutical distribution.

The NDC, by federal regulation, is a 10-digit numeric code preceded with the letter N or letters NDC. It consists of three numeric fields of information: a source identification field, a product identification field, and a trade package field. The FDA assigns the labeler portion of the code, while the labeler assigns the product identification and trade package portions according to format standards.

The FDA originally assigned the source identification field as four digits, starting at 0002. The system was designed not to exceed a source identification field of 0999. When it became apparent to the FDA that the number of product sources applying for labeler codes would exceed 0999, they reformatted the source I.D. field to comprise a five-digit numeric field beginning with 10000.

The product identification and trade package fields together comprise five digits, with the product identification field being three or four digits and the trade package field being two or one.

The NDC is presented in one of three formats: 4-4-2, 5-3-2 or 5-4-1 referred to in order of the above-identified three fields. The first field of four or five numbers corresponds to the source identification field. The next field of three or four numbers corresponds to the product identification field. The final field of one or two numbers corresponds to the trade package field.

Whenever an NDC is printed, all leading, imbedded and trailing zeros must be included. Each of the three fields are typically separated by a hyphen when printed in a human readable fonn, for example, 51999-432-10 for a 5-3-2 NDC number.

In their catalogs and on price lists, manufacturers and labelers are encouraged to include NDC numbers for each listed item. Labelers are typically urged to discontinue use of internal or traditional list, order or product numbers, as these identifiers are not generic to the pharmaceutical industry.

Because the NDC is the single basic means of product identification for all pharmaceutical products, it is desirable to have the NDC numbers encoded into a bar code and labeled onto products. Therefor, drug manufacturers and labelers are urged to identify their drug products with an NDC and to encode this number in bar code formats. However, there are many different bar code types as shown by example in FIG. 1 and a growing number of applications for each. Problems have arisen in that the various bar code types have different character lengths which do not correspond to the ten-digit NDC number.

SUMMARY OF THE INVENTION

In one aspect, the invention relates to a system for accurately dispensing prescriptions in a pharmacy comprising a computer, a reader operably interconnected to the computer, at least one of the reader and the computer adapted to detect and read indicia, and a converter operably interconnected to at least one of the computer and the reader for converting read indicia into an NDC number. The reader preferably reads the indicia from at least one of a package containing pharmaceutical products and a prescription. The read indicia is thereby standardized to an NDC number to ensure accuracy during the dispensation of a prescriptions in the pharmacy.

In various embodiments, the reader can comprise a scanner. The indicia can comprise a bar code. The converter can further comprise a database containing at least one table for converting the read indicia into an NDC number. Means for storing a first indicia and a second indicia can be provided as well as means for comparing the first indicia and the second indicia after both have been converted to NDC numbers by the converter. An alarm device for alerting an operator of the system can be employed if the an NDC number representing the first indicia does not match an NDC number representing the second indicia. The computer, reader and converter can be contained in a single housing.

In another aspect, the invention relates to a method of accurately dispensing prescriptions in a pharmacy having a computerized prescription dispensing system including a scanner and having an inventory of pharmaceutical products including the steps of: receiving a prescription for a patient identifying a desired pharmaceutical product and a desired dosage of the desired pharmaceutical product; entering first data representative of the prescription into the dispensing system; converting the first data into a first NDC number; retrieving the desired pharmaceutical product from the inventory; scanning a bar code on the desired pharmaceutical product with the scanner to convert the bar code into second data representative of the bar code; converting the second data into a second NDC number; and comparing the first NDC number with the second NDC number.

In various embodiments of the invention, the method can further comprise the step of alerting an operator of the pharmacy if the first NDC number does not equal the second NDC number. The method can also further comprise the step of dispensing the prescription to the patient if the first NDC number equals the second NDC number. A label can be printed describing the prescription for application to a container containing the dispensed prescription. The steps of scanning and converting to the first and second NDC numbers and the step of comparing the first and second NDC numbers can be performed internally of at least one of the computerized prescription dispensing system and the scanner. The method can further comprise the step of verifying the correct amount of the desired pharmaceutical product has been dispensed to the patient in accordance with the desired dosage. The first data can be used from a previously-dispensed prescription a refill label on a previously-dispensed patient refill bottle. The first data can be scanned from a bar code used for a previously-dispensed prescription.

BRIEF DESCRIPTION OF THE DRAWINGS

The invention will now be described with reference to the drawings wherein.

DESCRIPTION OF THE PREFERRED EMBODIMENTS

Figure 9:
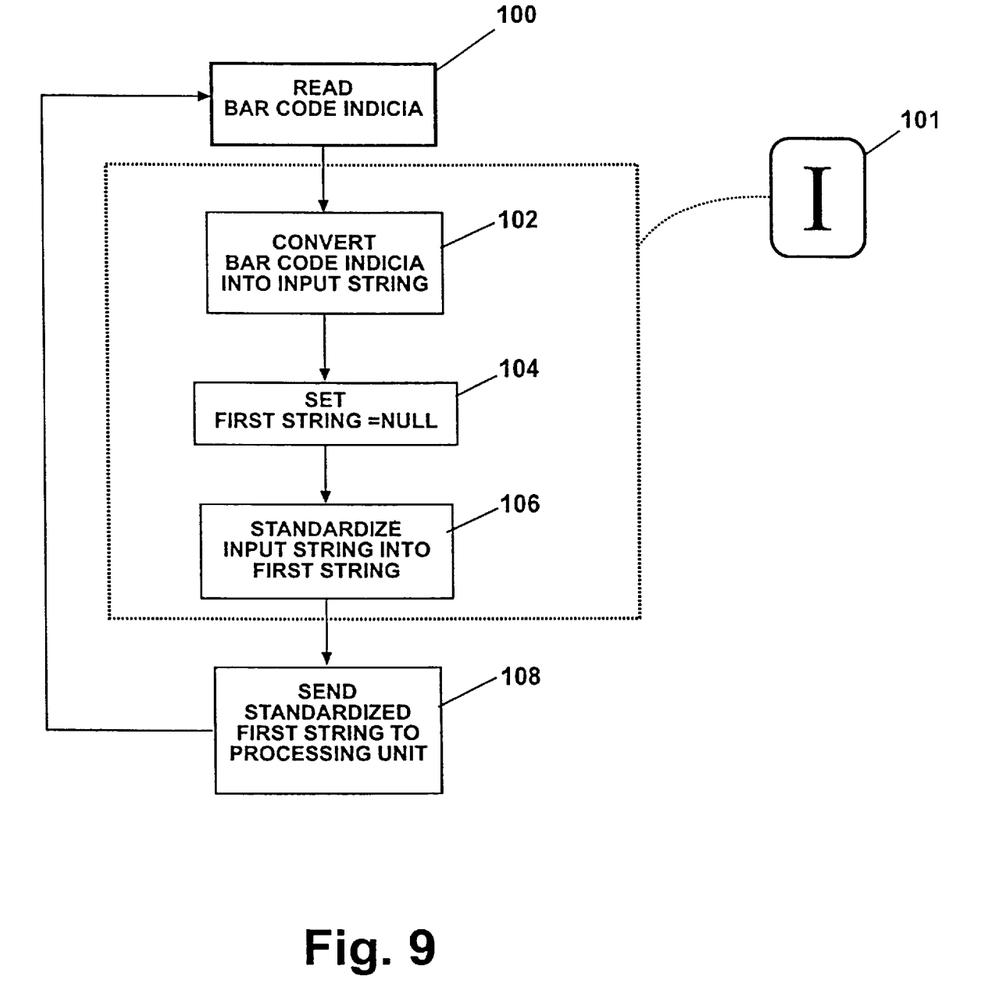
FIG. 9 is a flow chart illustrating the method of converting a bar code to a standardized NDC number.

The present invention comprises the converting of a bar code of any of the formats shown in FIG. 1 to a standardized 11-digit NDC number while simultaneously ensuring accurate entry of data relating to the pharmaceutical product into a computer system. As shown in FIG. 9, the first basic step 100 involves reading a bar code in the form of machine-readable data Such a bar code is typically found on the source's medication container. Bar codes on a source's bulk medication container can contain a bar code in a UPC symbol format or any of the other formats shown in FIG. 1. The manipulating of the data contained in the bar code into an NDC output format 101, comprises a step 102 of converting a bar code indicia into an input string, a step 104 of setting the first string to null, and a step 106 of standardizing the input string into a first string. Finally, as shown in step 108, the NDC output format 101 of the manipulated bar code is sent to a processing unit on a computer 38, as illustrated in FIG. 6. It will be understood that, although a particular scanning unit 40 and computer system 38 is disclosed in the drawings, any type of scanning unit having an internal or external connection to a processor can be used without departing from the scope of this invention. This includes a scanning device having all processing and memory elements contained in a unitary configuration or separate components, as shown in FIG. 6.

Figure 10:
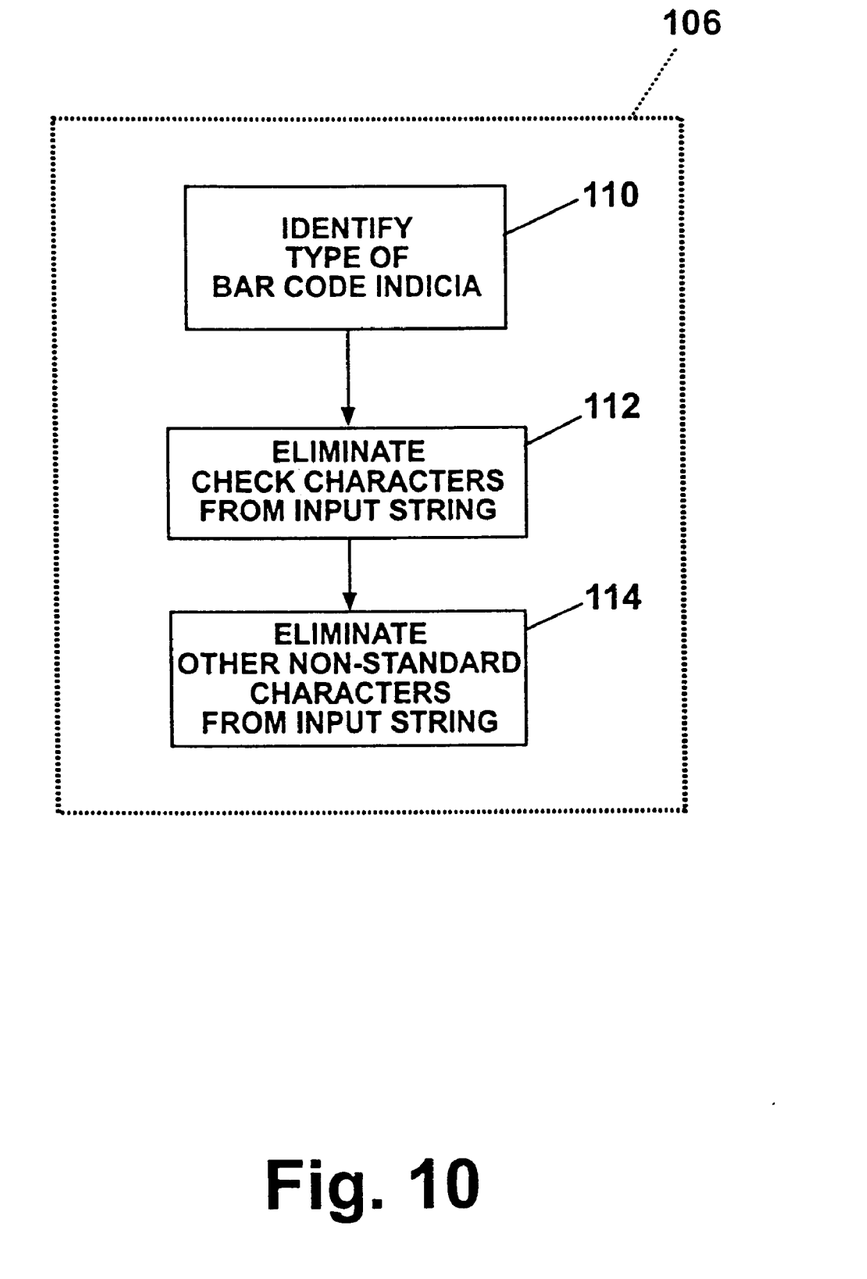
FIG. 10 is a flow chart illustrating the process of standardizing an input string into a first string.

The step 106 of standardizing an input string into a first string may be broken down into a number of additional steps illustrated in FIG. 10. First, as shown by step 110, the type of bar code must be identified. Second, as shown by step 112, any check digits present in the alphanumeric string read by the bar code must be eliminated. Third, any other digits not contained in an 11-digit NDC number must be eliminated as shown by step 114.

Figure 11:
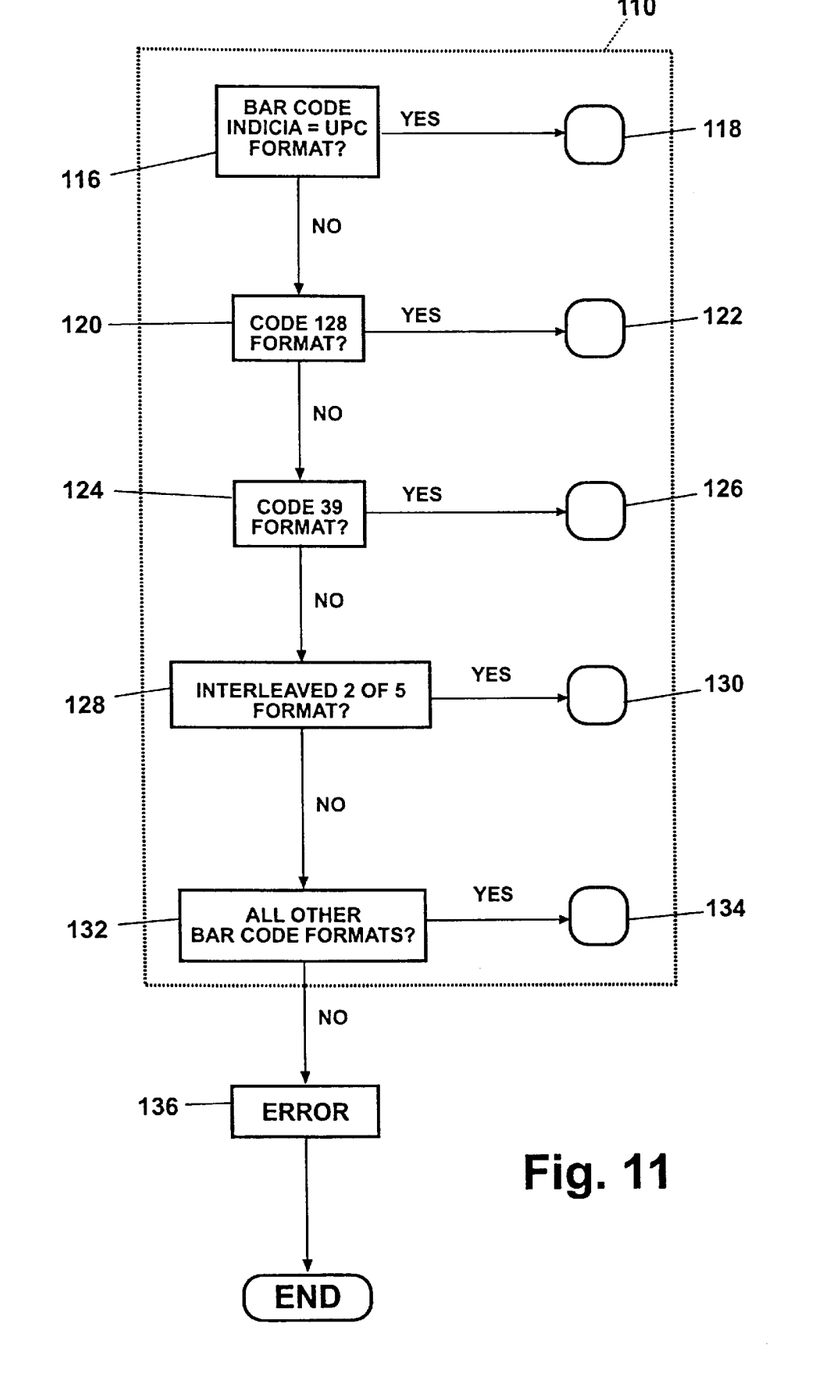
FIG. 11 is a flow chart illustrating the process for eliminating non-standard characters from the input string.

The following paragraphs outline the rules for converting a bar code into an NDC number depending upon the type of bar code read by a scanning device in accordance with a further breakdown of steps 110, 112, and 114. FIG. 11 in an expansion of step 110, wherein it will be understood that the scanning device has the ability to recognize a particular type of bar code.

Figure 13:
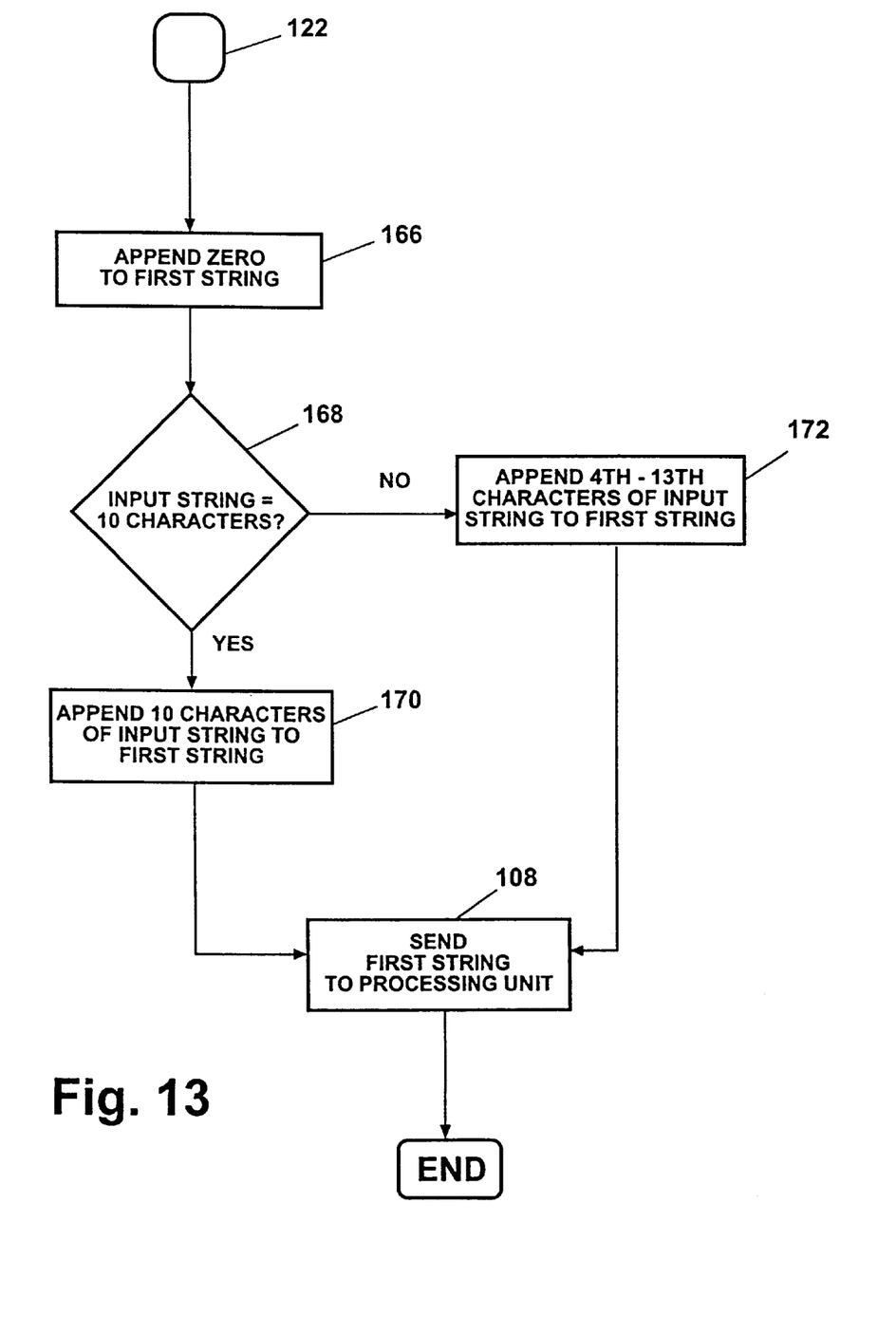
FIG. 13 is a flow chart illustrating the process of standardizing a bar code of Code 128 format.
Figure 14:
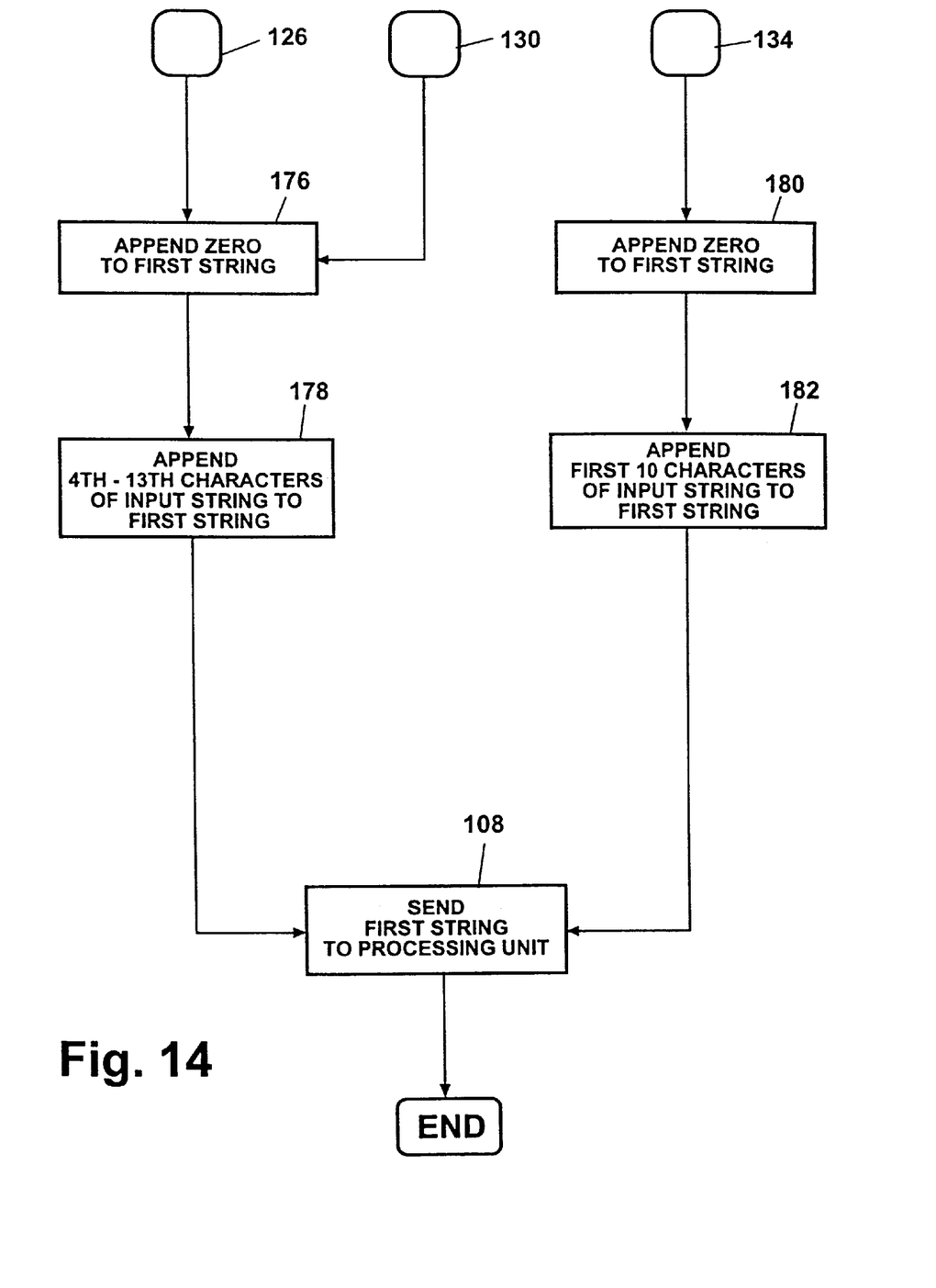
FIG. 14 is a flow chart illustrating the process of standardizing a bar code of Code 39, Interleaved 2 of 5, and other bar code formats.

At step 116, the device determines if the bar code indicia is equal to UPC format. If it is, then the formatting rules for the UPC format are followed at block 118 as illustrated in greater detail in FIG. 12. Alternatively, at step 120, if the bar code indicia is Code 128 format then the formatting rules for the Code 128 format are followed at block 122 as illustrated in greater detail in FIG. 13. If the bar code indicia is instead of Code 39 format as determined at step 124, then the formatting rules for the Code 39 format are followed at block 126 as shown in greater detail in FIG. 14. At step 128, the device determines if the bar code Indicia is of Interleaved 2 of 5 format. If so, then the formatting rules of block 130 are followed as also shown in FIG. 14. Finally, at step 132 the device determines if the bar code indicia are of any other recognized format. If so, then the formatting rules represented by block 134 are followed. Thus, the device calls upon one of the following format rules represented by blocks 118, 122, 126, 130, or 134, respectively, depending upon the type of bar code read. If the particular type of bar code cannot be recognized, the system returns an error at point 136 and the process ends.

Figure 12:
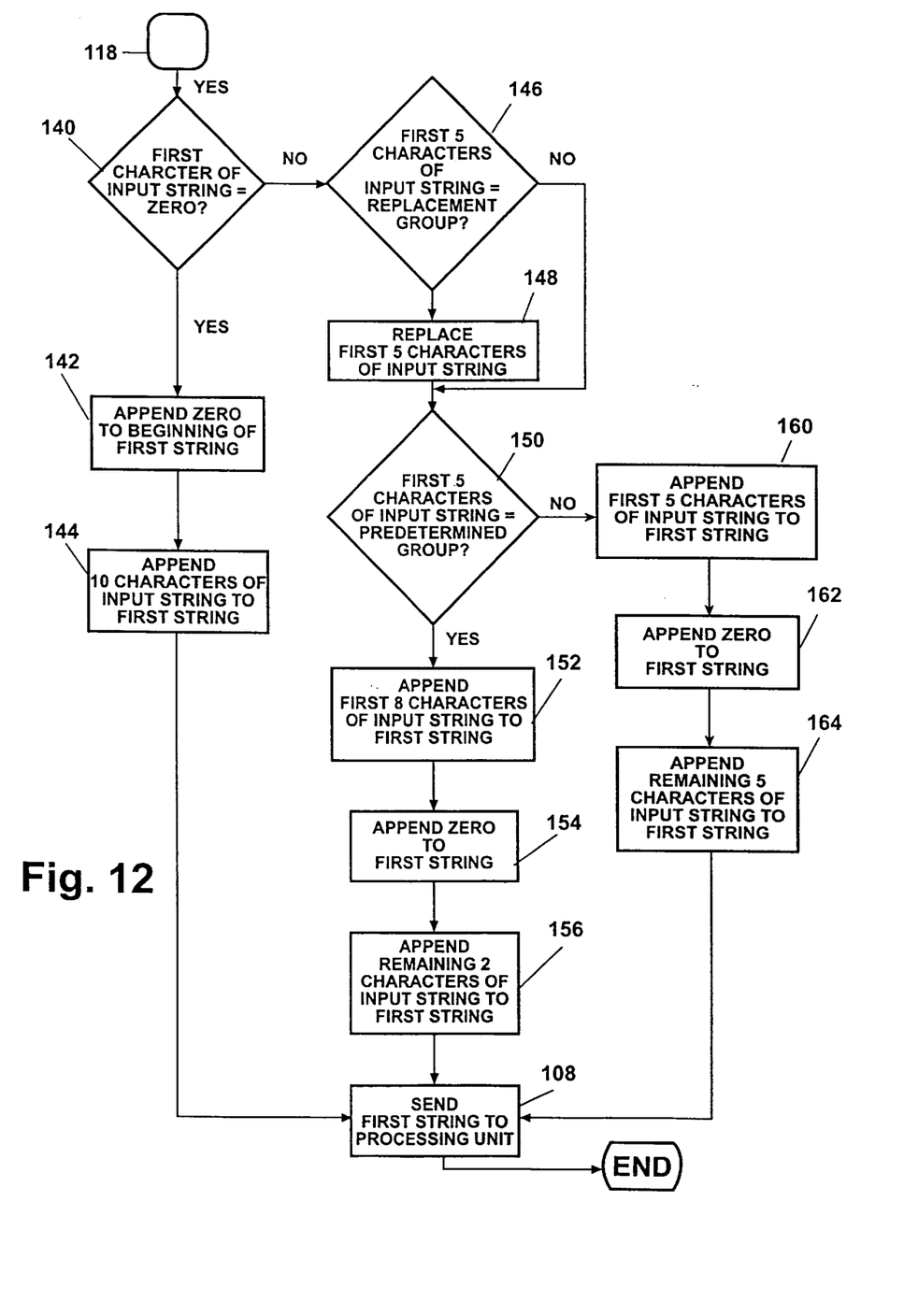
FIG. 12 is a flow chart illustrating the process of standardizing a bar code of UPC format.

For a UPC formatted bar code represented by block 118, the scanner reads the bar code at step 100 and converts it into an input string of the ten digits contained in a UPC bar code at step 102. Then to standardize the input string into a first string in a break down of steps 112 and 114, the specific approach illustrated in FIG. 12 is utilized. The first or lead character of the inputted string is identified at decision point 140. If the first character is a zero, then a zero is inserted at the beginning of the bar code at 142 and the ten characters of the alphanumeric string are appended thereto at 144 and sent to the process unit as shown by step 108. If the lead character is not a zero, then at decision point 146 the device determines if the first five characters of the input string are a replacement group. If the answer is no, then the device determines at decision point 150 if the first five characters in the alphanumeric string read by the scanning device are a predetermined group of, such as, but not limited to, 59911, 51875, 59930, 59762, 58634, 51672, 59366, or 59772. If the answer is yes, then the device sends the first eight digits of the inputted alphanumeric string from the bar code as shown by point 152, then a zero as shown by point 154, and then the remaining two characters of the alphanumeric string as shown by point 156 to create the first string. Then the first string is sent to the processing unit as shown by point 108.

If the first five characters of the input string comprise a replacement group at decision point 146, then the first five digits must be replaced with a substitute string as shown at point 148. For example, it has been found that if the first five digits are in the group of, but not limited to, 28176, 12899 and 47228, then the device must substitute the strings 51285, 55953 and 55053, respectively. This substitution is made for the purpose of converting a particular source's bar code to that source's NDC number. It will be understood that additional substitute NDC numbers can be provided in a database or other look-up table as required. Then, the process continues to decision step 150 as discussed above.

For UPC symbols wherein the first five characters of the input string are not a predetermined group at decision point 150, the scanning device will send the first five characters of the inputted string as shown at point 160, then a zero as shown at point 162, and then the remaining five characters of the UPC string as shown at point 164. Then the first string is sent to the processing unit as shown by point 108. Thus, in all cases, an 11-digit NDC number is produced and transmitted to the processing unit. For a code 128 formatted bar code represented by block 122, the scanner reads the bar code at step 100 and converts it into an input string. As shown in FIG. 13, for bar codes in Code 128 format, the bar codes typically produce either 10 or 15 alphanumeric characters when read by a scanning device. For a Code 128 bar code with 10 characters, the scanning device transmits a zero shown at step 166 followed by the ten digits of the inputted string. At decision point 168 the device confirms that the input string has 10 characters and then appends the ten characters of the input string to the first string at step 170. The first string is then sent to the processing unit as shown by step 108.

For bar codes in Code 128 format with 15 characters, the scanning device transmits a zero as shown at step 166, confirms that the input string has 15 characters at decision point 168 and then appends ten sequential characters of the input string beginning with the fourth character and ending with the thirteenth character as shown at step 172. The first string is then sent to the processing unit as shown by step 108.

For bar codes in Code 39 format represented by block 126, the scanner reads the bar code at step 100 and converts it into an input string. For bar codes in Code 39 format, the inputted alphanumeric string typically produces fifteen characters. As shown in FIG. 14, the scanning device transmits a zero as shown at point 176 in FIG. 14, followed by ten characters selected from the input alphanumeric string comprising the fourth through thirteenth characters therefrom as shown at point 178. The first string is then sent to the processing unit as shown by step 108.

For bar codes in Interleaved 2 of 5 format, represented by block 130, the bar codes typically produce a 14-character alphanumeric string. For these types of bar codes, the scanner reads the bar code at step 100 and converts it into an input string. The scanning device transmits a zero as shown at step 176, followed by the fourth through thirteenth characters in the inputted alphanumeric string as shown at point 178. The first string is then sent to the processing unit as shown by step 108.

For all other bar codes, represented by block 134 in FIG. 14, the scanning device transmits a zero as shown at step 180, followed by the first ten characters of the inputted alphanumeric string as shown by step 182 to form the 11-digit NDC number. Once again, the first string is then sent to the processing unit as shown by step 108.

A second embodiment of a method according to this invention compares a bar code on a source's pharmaceutical container with a bar code on a patient's prescription bottle, receipt or prescription which was printed by a pharmacy or doctor's office to verify that a correct prescription was dispensed.

Figure 15:
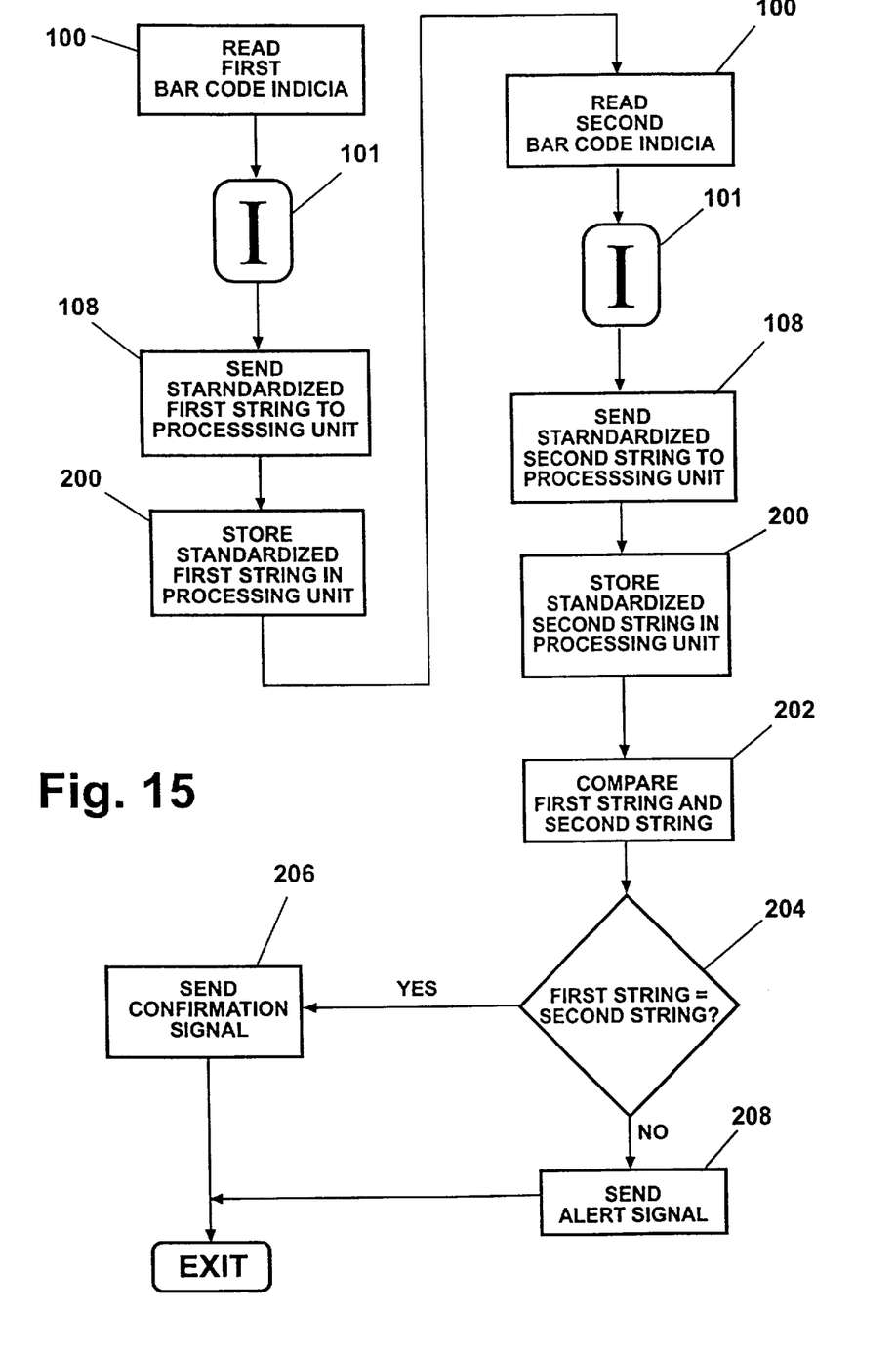
FIG. 15 illustrates a second method of comparing two bar code indicia.

As illustrated in FIG. 15, the second embodiment of a method comprises the step 100 of reading a first bar code from a first label. The first bar code is manipulated into an NDC output format or number 101 by the first embodiment of the method outlined above. The NDC number 101 is transmitted to the processing unit as shown by step 108 described above. The number 101 is then stored therein as shown at point 200. A second bar code is read from a label from a different container or prescription bottle or receipt by means of step 100. The second bar code is also manipulated into an NDC number 101 and transmitted to the processing unit as shown by the repetition of steps 108 and 200. The first and second manipulated NDC numbers 101 are then compared at step 202 to determine whether they match. As shown at decision point 204, if the first and second NDC numbers 101 match, a confirmation signal 206 is sent. Alternatively, an alert signal 208 is sent.

It will be understood that the processing unit can be located in a conventional computer workstation as described in the Background section or, alternatively, located in the scanning unit itself. For the latter option, greater convenience can be had by the operator because the scanning mechanism and processing unit are located in a single housing.

Thus, bar codes in varying formats from different sources can be converted into a standard NDC number and compared to determine whether the pharmaceutical products identified in each of the first and second bar codes are indeed the same product. It can thereby be verified that a patient has received a correct product and dosage. Otherwise, the pharmacist or pharmacy technician will receive an alarm before an incorrect product is dispensed.

It is contemplated that the scanner employed in connection with this invention be any type of suitable scanner capable of reading bar code indicia into a processing unit. Further, it is also contemplated that the scanner employed in connection with this invention be capable of reading all of, but not limited to, the bar code types displayed in FIG. 1. These bar codes include typical one-dimensional bar codes such as code 39 and code 128, two-dimensional bar codes such as PDF 417, and fill height and truncated UPC-A-EAN-13 symbols as shown in FIG. 1. Further, it is also contemplated that the scanner can read new types of bar codes such as three-dimensional bar codes by means of an imaging mechanism incorporated into the scanner or other means currently known or developed.

This invention also addresses the problem of updating a scanner's memory to reflect recent changes or additions to frequently changing bar code conversion information or routines stored in the scanner. Scanning devices, such as that shown as 40 in FIGS. 6–7, are typically provided with a memory chip (not shown) therein having a bank of random access memory (RAM) therein. Critical information, such as bar code recognition software and alphanumeric output programs, is loaded into the RAM and stored. Pharmaceutical suppliers and vendors often load information pertaining to recognition of specific bar code content as well, such as software which recognizes particular bar codes or a data bank of common bar codes.

As new bar code information becomes available, it must be downloaded into the RAM of the scanner 40. This process can be tedious, especially if a large volume or several smaller volumes of changes are required.

Figure 8:
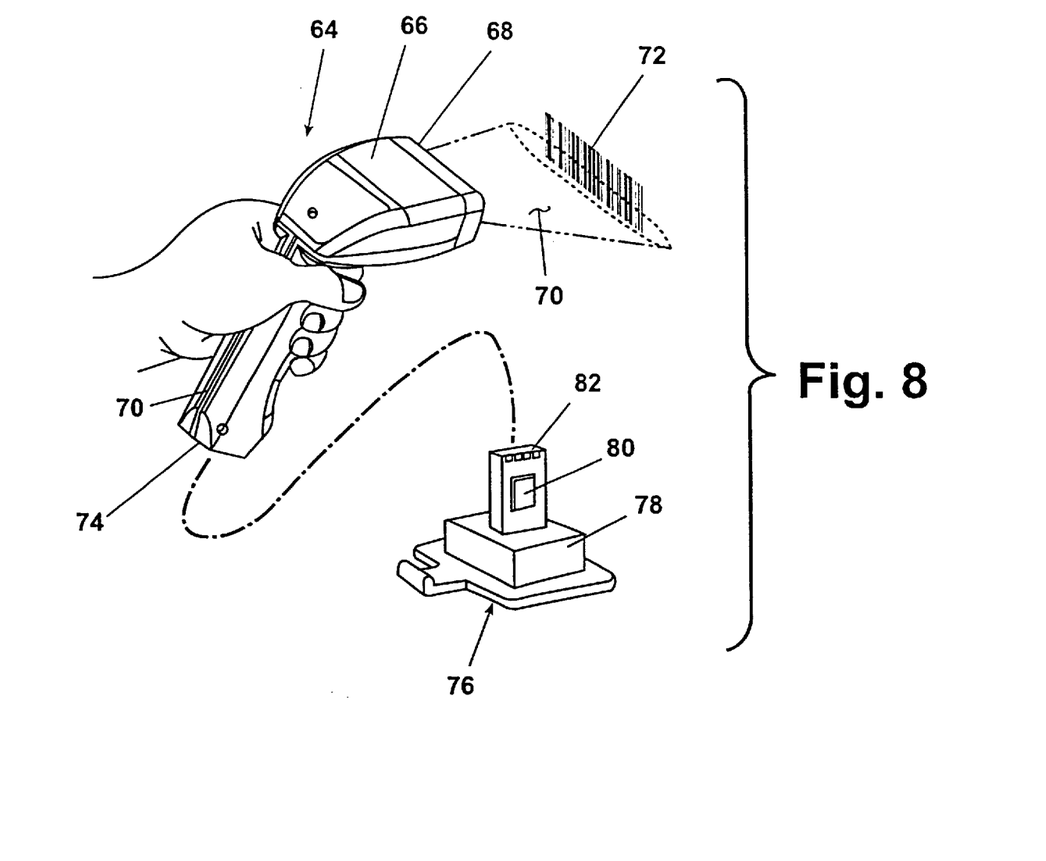
FIG. 8 is a perspective view of an improved scanning device according to the invention.

FIG. 8 shows an example of improved scanner 64 according to the invention which comprises a housing 66 having a laser port 68 and a handle 70. The scanner 64 is shown emitting a beam 70 over a bar code 72 as is conventionally done in the art. A distal end 74 of the handle 70 is provided with a removable panel 76 thereon. The panel 76 includes a substrate 78 which mounts a orthogonally-extending removable circuit 80 having a connector 82 thereon. The panel 76 is adapted to be inserted into the handle 70 and interconnected to the internal circuitry of the scanner 64 via the connector 82. The removable panel 76 can be positioned at any suitable location on the scanner 64 so that the panel 76 can be easily removed and does not interfere with any required connections to external components.

The circuit 80 is preferably a removable integrated circuit chip which can be removed and replaced with a new chip having any new bar code data stored thereon in addition to any older information to be retained. Thus, when new information becomes available, it can be mass produced in a new chip which thereby can be mounted to the panel 76 and inserted into the scanner 64. Thus, the need for a complicated reprogramming procedure for the scanner is eliminated.

While particular embodiments of the invention have been shown, it will be understood, of course, that the invention is not limited thereto since modifications may be made by those skilled in the art, particularly in light of the foregoing teachings. Reasonable variation and modification are possible within the scope of the foregoing disclosure of the invention without departing from the spirit of the invention.

What is claimed is:

1. A system for accurately dispensing prescriptions in a pharmacy comprising:

a processing unit;

a reader operably interconnected to the processing unit, at least one of the reader and the processing unit adapted to detect and read indicia on a pharmaceutical product source container containing a pharmaceutical product; and a converter operably interconnected to at least one of the processing unit and the reader for converting at least one of a manufacturer and a product indicia on the pharmaceutical product source container into an NDC number;

whereby when the converter converts the at least one of a manufacturer and a product indicia on a pharmaceutical product source container containing a pharmaceutical product into an NDC number, the indicia is standardized to an NDC number to ensure accuracy during the dispensation of a prescription for a product corresponding to the pharmaceutical product in the container having the same NDC number.

2. The system of claim 1 wherein the reader comprises a scanner.

3. The system of claim 2 wherein the indicia comprises a bar code.

4. The system of claim 3 wherein the converter further comprises a database containing at least one table for converting the read indicia into an NDC number.

5. The system of claim 4 and further comprising means for storing a first indicia and a second indicia and further comprising means for comparing the first indicia and the second indicia after both have been converted to NDC numbers by the converter.

6. The system of claim 5 and further comprising an alarm device for alerting an operator of the system if the an NDC number representing the first indicia does not match an NDC number representing the second indicia.

7. The system of claim 6 wherein the processing unit, reader and converter are contained in a single housing.

8. The system of claim 1 wherein the indicia comprises a bar code.

9. The system of claim 1 wherein the converter further comprises a database containing at least one table for converting the read indicia into an NDC number.

10. The system of claim 1 and further comprising means for storing a first indicia and a second indicia and further comprising means for comparing the first indicia and the second indicia after both have been converted to NDC numbers by the converter.

11. The system of claim 10 and further comprising an alarm device for alerting an operator of the system if the an NDC number representing the first indicia does not match an NDC number representing the second indicia.

12. The system of claim 1 wherein the processing unit, reader and converter are contained in a single housing.

13. A method of accurately dispensing prescriptions in a pharmacy having a computerized prescription dispensing system including a reader and having an inventory of pharmaceutical products including the steps of:

receiving a prescription for a patient identifying a desired pharmaceutical product and a desired dosage of the desired pharmaceutical product;

entering first data representative of the prescription into the dispensing system;

converting the first data into a first NDC number;

retrieving the desired pharmaceutical product source container from the inventory, said pharmaceutical product source container having at least one of a manufacturer and a product indicia;

reading the at least one of a manufacturer and a product indicia from the desired pharmaceutical product source container with the reader to convert the indicia into second data representative of the at least one of a manufacturer and a product indicia;

converting the second data into a second NDC number; and comparing the first NDC number with the second NDC number.

14. The method of claim 13 and further comprising the step of alerting an operator of the pharmacy if the first NDC number does not equal the second NDC number.

15. The method of claim 14 and further comprising the step of dispensing the prescription to the patient if the first NDC number equals the second NDC number.

16. The method of claim 15 and further comprising the step of printing a label describing the prescription for application to a container containing the dispensed prescription.

17. The method of claim 16 wherein the steps of scanning and converting to the first and second NDC numbers and the step of comparing the first and second NDC numbers are performed internally of at least one of the computerized prescription dispensing system and the reader.

18. The method of claim 17 and further comprising the step of verifying the correct amount of the desired pharmaceutical product has been dispensed to the patient in accordance with the desired dosage.

19. The method of claim 18 wherein the first data is provided on a container used for a previously-dispensed prescription a refill label on a previously-dispensed patient refill bottle.

20. The method of claim 13 and further comprising the step of dispensing the prescription to the patient if the first NDC number equals the second NDC number.

21. The method of claim 13 and further comprising the step of printing a label describing the prescription for application to a container containing the dispensed prescription.

22. The method of claim 13 wherein the steps of scanning and converting to the first and second NDC numbers and the step of comparing the first and second NDC numbers are performed internally of at least one of the computerized prescription dispensing system and the reader.

23. The method of claim 13 and further comprising the step of verifying the correct amount of the desired pharmaceutical product has been dispensed to the patient.

24. The method of claim 13 wherein the first data is scanned from a bar code used for a previously-dispensed prescription.

* * * * *

UNITED STATES PATENT AND TRADEMARK OFFICE
CERTIFICATE OF CORRECTION

PATENT NO.    : 6,260,761 B1                                               Page 1 of 1
DATED         : July 17, 2001
INVENTOR(S)   : Max J. Peoples, Jr.

It is certified that error appears in the above-identified patent and that said Letters Patent is hereby corrected as shown below:

Column 9,
Line 14, "the an NDC" should read -- the NDC --.
Lines 10-11, "the an NDC" should read -- the NDC --.

Column 10,
Line 30, "prescription a refill" should read -- prescription or a refill --.

Signed and Sealed this

Eleventh Day of June, 2002

Attest:

JAMES E. ROGAN
Attesting Officer            Director of the United States Patent and Trademark Office

(12) EX PARTE REEXAMINATION CERTIFICATE (5693rd)
United States Patent
Peoples, Jr.

(10) Number: US 6,260,761 C1
(45) Certificate Issued: Mar. 6, 2007

(54) SYSTEM AND METHOD FOR ACCURATELY DISPENSING PRESCRIPTIONS IN A PHARMACY

(76) Inventor: Max J. Peoples, Jr., 2737 Cooper Ridge Rd., Columbus, OH (US) 43231

Reexamination Request:
No. 90/007,117, Jul. 13, 2004

Reexamination Certificate for:
Patent No.: 6,260,761
Issued: Jul. 17, 2001
Appl. No.: 09/527,651
Filed: Mar. 17, 2000

Certificate of Correction issued Jun. 11, 2002.

Related U.S. Application Data (63) Continuation of application No. 09/085,279, filed on May 27, 1998, now Pat. No. 6,098,892.
(60) Provisional application No. 60/048,124, filed on May 30, 1997.

(51) Int. Cl.
*G08C 21/00* (2006.01)

(52) U.S. Cl. .................................. 235/462.07; 235/375
(58) Field of Classification Search .................. None
See application file for complete search history.

(56) References Cited

U.S. PATENT DOCUMENTS

| | | | |
|---|---|---|---|
| 3,921,196 A | 11/1975 | Patterson | |
| 4,476,381 A | 10/1984 | Rubin | |
| 4,818,850 A | 4/1989 | Gombrich et al. | |
| 4,835,372 A | 5/1989 | Gombrich et al. | |
| 4,879,456 A | 11/1989 | Cherry et al. | |
| 4,918,604 A * | 4/1990 | Baum | 221/5 |
| 4,929,818 A * | 5/1990 | Bradbury et al. | 235/381 |
| 5,208,762 A | 5/1993 | Charhut et al. | |
| 5,227,617 A | 7/1993 | Christopher et al. | |
| 5,262,625 A | 11/1993 | Tom et al. | |
| 5,283,699 A | 2/1994 | Komai et al. | |
| 5,337,919 A | 8/1994 | Spaulding et al. | |
| 5,401,059 A | 3/1995 | Ferrario | |
| 5,481,098 A | 1/1996 | Davis et al. | |
| 5,502,944 A | 4/1996 | Kraft et al. | |
| 5,569,899 A | 10/1996 | Tedesco | |
| 5,597,995 A | 1/1997 | Williams et al. | |
| 5,604,516 A | 2/1997 | Herrod et al. | |
| 5,700,998 A | 12/1997 | Palti | |
| 5,713,485 A | 2/1998 | Liff et al. | |
| 5,720,154 A * | 2/1998 | Lasher et al. | 53/411 |
| 5,739,518 A | 4/1998 | Wang | |
| 5,797,515 A | 8/1998 | Liff et al. | |
| 5,883,370 A | 3/1999 | Walker et al. | |
| 5,915,089 A * | 6/1999 | Stevens et al. | 709/202 |

FOREIGN PATENT DOCUMENTS

WO    WO 95/00427    1/1995

OTHER PUBLICATIONS

Author: Palmer, Roger C., Title: The Bar Code Book, 1991, Publisher: Helmers Publishing, Inc. Edition: Second Edition Pertinent pp: 69–76.*
"Bar Codes and Their Potential Applications in Hospital Pharmacy," Nold et al., American Journal of Hospital Pharmacy, vol. 42, Dec. 1985, pp. 2722–2732.
"The Health Industry Bar Code (HIBC) Supplier Labeling Standard, ANSI/HIBC 2–1997," American National Standards Institute, Inc., published Apr. 12, 1994, approved Apr. 29, 1997.

* cited by examiner

*Primary Examiner*—Margaret Rubin (57) ABSTRACT

A device and method is provided for converting product-specific identification numbers associated with bar code indicia on pharmaceutical products to an industry standard identification number. The process involves reading a bar code indicia, converting the indicia into an input string and standardizing the input string by means of adding or subtracting characters in accordance with rules based on the bar code type and length of the input string. By means of the invention pharmaceutical products of two different sources may be compared to determine if they contain the same drug as determined by the standard identification number. The device can include a removable member for interchanging and updating bar code indicia information rather than reprogramming the device.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–24 is confirmed.

* * * * *